(12) United States Patent
Lentzen (10) Patent No.: US 10,722,553 B2
(45) Date of Patent: Jul. 28, 2020

(54) MEDICAMENT CONTAINING RECOMBINANT MISTLETOE LECTINS FOR THE TREATMENT OF BRAIN TUMORS

(71) Applicant: Melema Pharma GmbH, Hamburg (DE)

(72) Inventor: Hans Lentzen, Rösrath (DE)

(73) Assignee: Melema Pharma GmbH, Hamburg (DE)

( * ) Notice: Subject to any disclaimer, the term of this patent is extended or adjusted under 35 U.S.C. 154(b) by 0 days.

(21) Appl. No.: 16/077,512

(22) PCT Filed: Feb. 15, 2017

(86) PCT No.: PCT/EP2017/053429
§ 371 (c)(1),
(2) Date: Aug. 13, 2018

(87) PCT Pub. No.: WO2017/140739
PCT Pub. Date: Aug. 24, 2017

(65) Prior Publication Data
US 2019/0046606 A1    Feb. 14, 2019

(30) Foreign Application Priority Data

Feb. 15, 2016    (EP) .................................... 16155735

(51) Int. Cl.
| | | |
|---|---|---|
| *A61K 38/16* | (2006.01) | |
| *A61K 45/06* | (2006.01) | |
| *C07K 14/42* | (2006.01) | |
| *A61P 35/00* | (2006.01) | |
| *A61K 36/185* | (2006.01) | |

(52) U.S. Cl.
CPC .......... *A61K 38/168* (2013.01); *A61K 36/185* (2013.01); *A61P 35/00* (2018.01); *C07K 14/42* (2013.01)

(58) Field of Classification Search
CPC .... A61K 38/16; A61K 38/185; A61K 38/168; A61K 45/06; A61P 35/00; C07K 14/42
USPC .... 514/300, 370, 19.2, 19.3, 21.2; 530/19.2, 530/19.3, 21.2, 300, 370
See application file for complete search history.

(56) References Cited

U.S. PATENT DOCUMENTS

| | | | | |
|---|---|---|---|---|
| 6,271,368 B1 * | 8/2001 | Lentzen | ............. | A61K 47/6819 536/23.6 |
| 7,635,567 B2 | 12/2009 | Müthing et al. | | |
| 9,981,007 B2 | 5/2018 | Lentzen et al. | | |
| 2005/0221380 A1 * | 10/2005 | Muthing | ................ | C07K 16/18 435/7.1 |

FOREIGN PATENT DOCUMENTS

| | | |
|---|---|---|
| EP | 2508195 A1 | 10/2012 |
| WO | WO-03054544 A2 | 7/2003 |

OTHER PUBLICATIONS

Gabius, H-J., et al., "The Immunomodulatory ?-Galactoside-Specific Lectin from Mistletoe: Partial Sequence Analysis, Cell and Tissue Binding, and Impact on Intracellular Biosignalling of Monocytic Leukemia Cells", Anticancer Research, vol. 12, No. 3, (1992), pp. 669-675.
International Search Report for PCT/EP2017/053429 dated Jun. 7, 2017.
Schötterl, S., et al., "Mistletoe Compounds as Anti-Cancer Drugs: Effects and Mechanisms in the Treatment of Glioblastoma". In *Mistletoe: From Mythology to Evidence-Based Medicine*; Zänker, K., Kaveri, S. (eds.); Karger: Basel, 2015; vol. 4; pp. 48-56.
Written Opinion of the International Searching Authority for PCT/EP2017/053429 dated Jun. 7, 2017.
Zuzak, T.J., et al., "Paediatric Medulloblastoma Cells are Susceptible to *Viscum Album* (Mistletoe) Preparations", Anticancer Research, vol. 26, No. 5A, (2006), pp. 3485-3492.

* cited by examiner

*Primary Examiner* — Julie Ha
(74) *Attorney, Agent, or Firm* — Faegre Drinker Biddle & Reath LLP (57) ABSTRACT

Methods of treating a brain tumor by administering a drug containing recombinant mistletoe lectin are described. The recombinant mistletoe lectin can be a mistletoe lectin A-chain, a mistletoe lectin B-chain, or a combination thereof. Brain tumors that can be treated by the method described include primary brain tumours, gliomas, glioblastomas, meningiomas and pituitary adenomas.

11 Claims, 1 Drawing Sheet
Specification includes a Sequence Listing.

```
                        SEQUENCE LISTING

<160> NUMBER OF SEQ ID NOS: 12

<210> SEQ ID NO 1
<211> LENGTH: 253
<212> TYPE: PRT
<213> ORGANISM: Artificial Sequence
<220> FEATURE:
<223> OTHER INFORMATION: Recombinant protein (EP0751221)
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (5)..(5)
<223> OTHER INFORMATION: Xaa can be Ile or Leu
<220> FEATURE:
<221> NAME/KEY: misc_feature
<222> LOCATION: (16)..(16)
<223> OTHER INFORMATION: Xaa can be Glu or Asp

<400> SEQUENCE: 1

Xaa Tyr Glu Arg Xaa Arg Leu Arg Val Thr His Gln Thr Thr Gly Xaa
1               5                   10                  15

Glu Tyr Phe Arg Phe Ile Thr Leu Leu Arg Asp Tyr Val Ser Ser Gly
                20                  25                  30

Ser Phe Ser Asn Glu Ile Pro Leu Leu Arg Gln Ser Thr Ile Pro Val
            35                  40                  45

Ser Asp Ala Gln Arg Phe Val Leu Val Glu Leu Thr Asn Gln Gly Gly
        50                  55                  60

Asp Ser Ile Thr Ala Ala Ile Asp Val Thr Asn Leu Tyr Val Val Ala
65                  70                  75                  80

Tyr Gln Ala Gly Asp Gln Ser Tyr Phe Leu Arg Asp Ala Pro Arg Gly
                85                  90                  95

Ala Glu Thr His Leu Phe Thr Gly Thr Thr Arg Ser Ser Leu Pro Phe
            100                 105                 110

Asn Gly Ser Tyr Pro Asp Leu Glu Arg Tyr Ala Gly His Arg Asp Gln
        115                 120                 125

Ile Pro Leu Gly Ile Asp Gln Leu Ile Gln Ser Val Thr Ala Leu Arg
130                 135                 140

Phe Pro Gly Gly Ser Thr Arg Thr Gln Ala Arg Ser Ile Leu Ile Leu
145                 150                 155                 160

Ile Gln Met Ile Ser Glu Ala Ala Arg Phe Asn Pro Ile Leu Trp Arg
                165                 170                 175

Ala Arg Gln Tyr Ile Asn Ser Gly Ala Ser Phe Leu Pro Asp Val Tyr
            180                 185                 190

Met Leu Glu Leu Glu Thr Ser Trp Gly Gln Gln Ser Thr Gln Val Gln
        195                 200                 205

His Ser Thr Asp Gly Val Phe Asn Asn Pro Ile Arg Leu Ala Ile Pro
    210                 215                 220

Pro Gly Asn Phe Val Thr Leu Thr Asn Val Arg Asp Val Ile Ala Ser
225                 230                 235                 240
```

Leu Ala Ile Met Leu Phe Val Cys Gly Glu Arg Pro Ser
                245                 250

<210> SEQ ID NO 2
<211> LENGTH: 257
<212> TYPE: PRT
<213> ORGANISM: Artificial Sequence
<220> FEATURE:
<223> OTHER INFORMATION: Recombinant protein (EP1051495)
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (16)..(16)
<223> OTHER INFORMATION: Xaa can be Asp or Glu
<220> FEATURE:
<221> NAME/KEY: misc_feature
<222> LOCATION: (64)..(64)
<223> OTHER INFORMATION: Xaa can be Gly or Gln
<220> FEATURE:
<221> NAME/KEY: misc_feature
<222> LOCATION: (67)..(67)
<223> OTHER INFORMATION: Xaa can be Ile or Val
<220> FEATURE:
<221> NAME/KEY: misc_feature
<222> LOCATION: (76)..(76)
<223> OTHER INFORMATION: Xaa can be Leu or Ala
<220> FEATURE:
<221> NAME/KEY: misc_feature
<222> LOCATION: (108)..(109)
<223> OTHER INFORMATION: Xaa can be Asp-Arg or can be deleted
<220> FEATURE:
<221> NAME/KEY: misc_feature
<222> LOCATION: (115)..(115)
<223> OTHER INFORMATION: Xaa can be Asn or Thr
<220> FEATURE:
<221> NAME/KEY: misc_feature
<222> LOCATION: (119)..(119)
<223> OTHER INFORMATION: Xaa can be Pro or Thr
<220> FEATURE:
<221> NAME/KEY: misc_feature
<222> LOCATION: (136)..(136)
<223> OTHER INFORMATION: Xaa can be Asp or Glu
<220> FEATURE:
<221> NAME/KEY: misc_feature
<222> LOCATION: (143)..(143)
<223> OTHER INFORMATION: Xaa can be Ser or Thr
<220> FEATURE:
<221> NAME/KEY: misc_feature
<222> LOCATION: (147)..(147)
<223> OTHER INFORMATION: Xaa can be Phe or Tyr
<220> FEATURE:
<221> NAME/KEY: misc_feature
<222> LOCATION: (154)..(154)
<223> OTHER INFORMATION: Xaa can be Ala or Thr
<220> FEATURE:
<221> NAME/KEY: misc_feature
<222> LOCATION: (179)..(179)
<223> OTHER INFORMATION: Xaa can be Ala or Tyr
<220> FEATURE:
<221> NAME/KEY: misc_feature
<222> LOCATION: (182)..(182)
<223> OTHER INFORMATION: Xaa can be Tyr or Asp
<220> FEATURE:
<221> NAME/KEY: misc_feature
<222> LOCATION: (187)..(187)
<223> OTHER INFORMATION: Xaa can be Ala or Glu
<220> FEATURE:
<221> NAME/KEY: misc_feature
<222> LOCATION: (193)..(193)
<223> OTHER INFORMATION: Xaa can be Val or Met
<220> FEATURE:
<221> NAME/KEY: misc_feature
<222> LOCATION: (221)..(221)
<223> OTHER INFORMATION: Xaa can be Ile or Phe
<220> FEATURE:

<220> FEATURE:
<221> NAME/KEY: misc_feature
<222> LOCATION: (227)..(227)
<223> OTHER INFORMATION: Xaa can be Ser or Thr
<220> FEATURE:
<221> NAME/KEY: misc_feature
<222> LOCATION: (234)..(234)
<223> OTHER INFORMATION: Xaa can be Thr or Ser
<220> FEATURE:
<221> NAME/KEY: misc_feature
<222> LOCATION: (238)..(238)
<223> OTHER INFORMATION: Xaa can be Asp or Ser
<220> FEATURE:
<221> NAME/KEY: misc_feature
<222> LOCATION: (256)..(257)
<223> OTHER INFORMATION: Xaa can be Ser-Ser or can be deleted

<400> SEQUENCE: 2

```
Xaa Tyr Glu Arg Leu Arg Leu Arg Val Thr His Gln Thr Thr Gly Xaa
1               5                   10                  15

Glu Tyr Phe Arg Phe Ile Thr Leu Leu Arg Asp Tyr Val Ser Ser Gly
            20                  25                  30

Ser Phe Ser Asn Glu Ile Pro Leu Leu Arg Gln Ser Thr Ile Pro Val
        35                  40                  45

Ser Asp Ala Gln Arg Phe Val Leu Val Glu Leu Thr Asn Gln Gly Xaa
50                  55                  60

Asp Ser Xaa Thr Ala Ala Ile Asp Val Thr Asn Xaa Tyr Val Val Ala
65                  70                  75                  80

Tyr Gln Ala Gly Asp Gln Ser Tyr Phe Leu Arg Asp Ala Pro Arg Gly
                85                  90                  95

Ala Glu Thr His Leu Phe Thr Gly Thr Thr Arg Xaa Xaa Ser Ser Leu
            100                 105                 110

Pro Phe Xaa Gly Ser Tyr Xaa Asp Leu Glu Arg Tyr Ala Gly His Arg
        115                 120                 125

Asp Gln Ile Pro Leu Gly Ile Xaa Gln Leu Ile Gln Ser Val Xaa Ala
130                 135                 140

Leu Arg Xaa Pro Gly Gly Ser Thr Arg Xaa Gln Ala Arg Ser Ile Leu
145                 150                 155                 160

Ile Leu Ile Gln Met Ile Ser Glu Ala Ala Arg Phe Asn Pro Ile Leu
                165                 170                 175

Trp Arg Xaa Arg Gln Xaa Ile Asn Ser Gly Xaa Ser Phe Leu Pro Asp
            180                 185                 190

Xaa Tyr Met Leu Glu Leu Glu Thr Ser Trp Gly Gln Ser Thr Gln
        195                 200                 205

Val Gln His Ser Thr Asp Gly Val Phe Asn Pro Xaa Arg Leu Ala
    210                 215                 220

Ile Pro Xaa Gly Asn Phe Val Thr Leu Xaa Asn Val Arg Xaa Val Ile
225                 230                 235                 240

Ala Ser Leu Ala Ile Met Leu Phe Val Cys Gly Glu Arg Pro Ser Xaa
                245                 250                 255

Xaa
```

<210> SEQ ID NO 3
<211> LENGTH: 257
<212> TYPE: PRT
<213> ORGANISM: Artificial Sequence
<220> FEATURE:
<223> OTHER INFORMATION: Recombinant protein (EP1051495)
<220> FEATURE:
<221> NAME/KEY: misc_feature
<222> LOCATION: (1)..(1)
<223> OTHER INFORMATION: Xaa can be Met or can be deleted

<400> SEQUENCE: 3

```
Xaa Tyr Glu Arg Leu Arg Leu Arg Val Thr His Gln Thr Thr Gly Asp
1               5                   10                  15

Glu Tyr Phe Arg Phe Ile Thr Leu Leu Arg Asp Tyr Val Ser Ser Gly
            20                  25                  30

Ser Phe Ser Asn Glu Ile Pro Leu Leu Arg Gln Ser Thr Ile Pro Val
        35                  40                  45

Ser Asp Ala Gln Arg Phe Val Leu Val Glu Leu Thr Asn Gln Gly Gln
    50                  55                  60

Asp Ser Ile Thr Ala Ala Ile Asp Val Thr Asn Ala Tyr Val Val Ala
65                  70                  75                  80

Tyr Gln Ala Gly Asp Gln Ser Tyr Phe Leu Arg Asp Ala Pro Arg Gly
                85                  90                  95

Ala Glu Thr His Leu Phe Thr Gly Thr Thr Arg Asp Arg Ser Ser Leu
            100                 105                 110

Pro Phe Thr Gly Ser Tyr Thr Asp Leu Glu Arg Tyr Ala Gly His Arg
        115                 120                 125

Asp Gln Ile Pro Leu Gly Ile Glu Gln Leu Ile Gln Ser Val Ser Ala
    130                 135                 140

Leu Arg Tyr Pro Gly Gly Ser Thr Arg Ala Gln Ala Arg Ser Ile Leu
145                 150                 155                 160

Ile Leu Ile Gln Met Ile Ser Glu Ala Ala Arg Phe Asn Pro Ile Leu
                165                 170                 175

Trp Arg Tyr Arg Gln Asp Ile Asn Ser Gly Glu Ser Phe Leu Pro Asp
            180                 185                 190

Met Tyr Met Leu Glu Leu Glu Thr Ser Trp Gly Gln Gln Ser Thr Gln
        195                 200                 205

Val Gln His Ser Thr Asp Gly Val Phe Asn Asn Pro Phe Arg Leu Ala
    210                 215                 220

Ile Ser Thr Gly Asn Phe Val Thr Leu Ser Asn Val Arg Ser Val Ile
225                 230                 235                 240

Ala Ser Leu Ala Ile Met Leu Phe Val Cys Gly Glu Arg Pro Ser Ser
                245                 250                 255

Ser
```

<210> SEQ ID NO 4
<211> LENGTH: 264
<212> TYPE: PRT
<213> ORGANISM: Artificial Sequence
<220> FEATURE:
<223> OTHER INFORMATION: Recombinant protein (EP0751221)
<220> FEATURE:
<221> NAME/KEY: misc_feature
<222> LOCATION: (1)..(1)
<223> OTHER INFORMATION: Xaa can be Met or can be deleted

<400> SEQUENCE: 4

```
Xaa Asp Asp Val Thr Cys Ser Ala Ser Glu Pro Thr Val Arg Ile Val
1               5                   10                  15

Gly Arg Asn Gly Met Cys Val Asp Val Arg Asp Asp Asp Phe Arg Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Gly Thr Ile Arg Ser Asn Gly Ser
    50                  55                  60
```

```
Cys Leu Thr Thr Tyr Gly Tyr Thr Ala Gly Val Tyr Val Met Ile Phe
 65                  70                  75                  80

Asp Cys Asn Thr Ala Val Arg Glu Ala Thr Leu Trp Gln Ile Trp Gly
                 85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Lys Asn Gln Arg Trp Ala
                165                 170                 175

Leu Tyr Gly Asp Gly Ser Ile Arg Pro Lys Gln Asn Gln Asp Gln Cys
            180                 185                 190

Leu Thr Cys Gly Arg Asp Ser Val Ser Thr Val Ile Asn Ile Val Ser
        195                 200                 205

Cys Ser Ala Gly Ser Ser Gly Gln Arg Trp Val Phe Thr Asn Glu Gly
210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Pro
            260
```

<210> SEQ ID NO 5
<211> LENGTH: 268
<212> TYPE: PRT
<213> ORGANISM: Artificial Sequence
<220> FEATURE:
<223> OTHER INFORMATION: Recombinant protein (EP0751221)
<220> FEATURE:
<221> NAME/KEY: misc_feature
<222> LOCATION: (1)..(1)
<223> OTHER INFORMATION: Xaa can be Met or can be deleted

<400> SEQUENCE: 5

```
Xaa Asp Asp Val Thr Cys Ser Ala Ser Glu Pro Thr Val Arg Ile Val
  1               5                  10                  15

Gly Arg Asn Gly Met Cys Val Asp Val Arg Asp Asp Asp Phe Arg Asp
             20                  25                  30

Gly Asn Gln Ile Gln Leu Trp Pro Ser Lys Ser Asn Asn Asp Pro Asn
         35                  40                  45

Gln Leu Trp Thr Ile Lys Arg Asp Gly Thr Ile Arg Ser Asn Gly Ser
     50                  55                  60

Cys Leu Thr Thr Tyr Gly Tyr Thr Ala Gly Val Tyr Val Met Ile Phe
 65                  70                  75                  80

Asp Cys Asn Thr Ala Val Arg Glu Ala Thr Leu Trp Gln Ile Trp Gly
                 85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
130                 135                 140
```

Thr Ile Tyr Gly Phe Arg Asp Leu Cys Met Glu Ser Asn Gly Gly Ser
145                 150                 155                 160

Val Trp Val Glu Thr Cys Val Ser Ser Gln Lys Asn Gln Arg Trp Ala
                165                 170                 175

Leu Tyr Gly Asp Gly Ser Ile Arg Pro Lys Gln Asn Gln Asp Gln Cys
            180                 185                 190

Leu Thr Cys Gly Arg Asp Ser Val Ser Thr Val Ile Asn Ile Val Ser
        195                 200                 205

Cys Ser Ala Gly Ser Ser Gly Gln Arg Trp Val Phe Thr Asn Glu Gly
    210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Pro Gly Gly Tyr His
                260                 265

<210> SEQ ID NO 6
<211> LENGTH: 265
<212> TYPE: PRT
<213> ORGANISM: Artificial
<220> FEATURE:
<223> OTHER INFORMATION: Recombinant protein (EP1051495)
<220> FEATURE:
<221> NAME/KEY: misc_feature
<222> LOCATION: (1)..(1)
<223> OTHER INFORMATION: Xaa can be Met or can be deleted
<220> FEATURE:
<221> NAME/KEY: misc_feature
<222> LOCATION: (19)..(19)
<223> OTHER INFORMATION: Xaa can be Asn or Ser
<220> FEATURE:
<221> NAME/KEY: misc_feature
<222> LOCATION: (22)..(22)
<223> OTHER INFORMATION: Xaa can be Cys or Arg
<220> FEATURE:
<221> NAME/KEY: misc_feature
<222> LOCATION: (57)..(57)
<223> OTHER INFORMATION: Xaa can be Gly or Asn
<220> FEATURE:
<221> NAME/KEY: misc_feature
<222> LOCATION: (96)..(96)
<223> OTHER INFORMATION: Xaa can be Gly or Asn
<220> FEATURE:
<221> NAME/KEY: misc_feature
<222> LOCATION: (158)..(158)
<223> OTHER INFORMATION: Xaa can be Gly or Gln
<220> FEATURE:
<221> NAME/KEY: misc_feature
<222> LOCATION: (167)..(167)
<223> OTHER INFORMATION: Xaa can be Val or Asp
<220> FEATURE:
<221> NAME/KEY: misc_feature
<222> LOCATION: (171)..(171)
<223> OTHER INFORMATION: Xaa can be Gln or Lys
<220> FEATURE:
<221> NAME/KEY: misc_feature
<222> LOCATION: (174)..(175)
<223> OTHER INFORMATION: Xaa is Gly, Gly-Arg, Gly-Lys, Arg, Lys or can
    be deleted
<220> FEATURE:
<221> NAME/KEY: misc_feature
<222> LOCATION: (196)..(196)
<223> OTHER INFORMATION: Xaa can be Cys or Val or Ser
<220> FEATURE:
<221> NAME/KEY: misc_feature
<222> LOCATION: (212)..(213)
<223> OTHER INFORMATION: Xaa can be Ala-Ala or Ala-Gly or Gly-Ala or
    Gly-Gly
<220> FEATURE:

```
<221> NAME/KEY: misc_feature
<222> LOCATION: (215)..(216)
<223> OTHER INFORMATION: Xaa can be Ser-Ser or Ser-Gly or Gly-Ser or
      Gly-Gly
<220> FEATURE:
<221> NAME/KEY: misc_feature
<222> LOCATION: (225)..(225)
<223> OTHER INFORMATION: Xaa can be Gly or Tyr
<220> FEATURE:
<221> NAME/KEY: misc_feature
<222> LOCATION: (232)..(236)
<223> OTHER INFORMATION: 232Asn,Ser,Thr,Lys;233Ser,Gly;234Leu,
      Pro;235Ala,Met;236:Met,Val
<220> FEATURE:
<221> NAME/KEY: misc_feature
<222> LOCATION: (265)..(265)
<223> OTHER INFORMATION: Xaa can be Pro or Phe

<400> SEQUENCE: 6

Xaa Asp Asp Val Thr Cys Ser Ala Ser Glu Pro Thr Val Arg Ile Val
1               5                   10                  15

Gly Arg Xaa Gly Met Xaa Val Asp Val Arg Asp Asp Phe His Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Xaa Thr Ile Arg Ser Asn Gly Ser
50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Xaa
            85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
            130                 135                 140

Thr Ile Tyr Gly Phe Arg Asp Leu Cys Met Glu Ser Asn Xaa Gly Ser
145                 150                 155                 160

Val Trp Val Glu Thr Cys Xaa Ser Ser Gln Xaa Asn Gln Xaa Xaa Trp
                165                 170                 175

Ala Leu Tyr Gly Asp Gly Ser Ile Arg Pro Lys Gln Asn Gln Asp Gln
            180                 185                 190

Cys Leu Thr Xaa Gly Arg Asp Ser Val Ser Thr Val Ile Asn Ile Val
            195                 200                 205

Ser Cys Ser Xaa Xaa Ser Xaa Xaa Gln Arg Trp Val Phe Thr Asn Glu
210                 215                 220

Xaa Ala Ile Leu Asn Leu Lys Xaa Xaa Xaa Xaa Asp Val Ala Gln
225                 230                 235                 240

Ala Asn Pro Lys Leu Arg Arg Ile Ile Ile Tyr Pro Ala Thr Gly Lys
            245                 250                 255

Pro Asn Gln Met Trp Leu Pro Val Xaa
            260                 265

<210> SEQ ID NO 7
<211> LENGTH: 264
<212> TYPE: PRT
<213> ORGANISM: Artificial
<220> FEATURE:
<223> OTHER INFORMATION: Recombinant protein (EP1051495)
<220> FEATURE:
```

<221> NAME/KEY: misc_feature
<222> LOCATION: (1)..(1)
<223> OTHER INFORMATION: Xaa can be Met or can be deleted

<400> SEQUENCE: 7

Xaa Asp Asp Val Thr Cys Ser Ala Ser Glu Pro Thr Val Arg Ile Val
1               5                   10                  15

Gly Arg Asn Gly Met Cys Val Asp Val Arg Asp Asp Phe His Asp
            20                  25                  30

Gly Asn Gln Ile Gln Leu Trp Pro Ser Lys Ser Asn Asn Asp Pro Asn
            35                  40                  45

Gln Leu Trp Thr Ile Lys Arg Asp Gly Thr Ile Arg Ser Asn Gly Ser
50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Gly
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
            115                 120                 125

Leu Gly Gln Gly Trp Leu Ala Gly Asn Asp Thr Ala Pro Arg Glu Val
130                 135                 140

Thr Ile Tyr Gly Phe Arg Asp Leu Cys Met Glu Ser Asn Gly Gly Ser
145                 150                 155                 160

Val Trp Val Glu Thr Cys Val Ser Ser Gln Gln Asn Gln Arg Trp Ala
                165                 170                 175

Leu Tyr Gly Asp Gly Ser Ile Arg Pro Lys Gln Asn Gln Asp Gln Cys
            180                 185                 190

Leu Thr Cys Gly Arg Asp Ser Val Ser Thr Val Ile Asn Ile Val Ser
            195                 200                 205

Cys Ser Ala Gly Ser Ser Gly Gln Arg Trp Val Phe Thr Asn Glu Gly
210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Pro
            260

<210> SEQ ID NO 8
<211> LENGTH: 265
<212> TYPE: PRT
<213> ORGANISM: Artificial
<220> FEATURE:
<223> OTHER INFORMATION: Recombinant protein (EP1051495)
<220> FEATURE:
<221> NAME/KEY: misc_feature
<222> LOCATION: (1)..(1)
<223> OTHER INFORMATION: Xaa can be Met or can be deleted

<400> SEQUENCE: 8

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
            35                  40                  45

-continued

```
Gln Leu Trp Thr Ile Lys Arg Asp Gly Thr Ile Arg Ser Asn Gly Ser
         50                  55                  60

Cys Leu Thr Thr Tyr Gly Tyr Thr Ala Gly Val Tyr Val Met Ile Phe
 65                  70                  75                  80

Asp Cys Asn Thr Ala Val Arg Glu Ala Thr Ile Trp Gln Ile Trp Asp
                 85                  90                  95

Asn Gly Thr Ile Ile Asn Pro Arg Ser Asn Leu Val Leu Ala Ala Ser
             100                 105                 110

Ser Gly Ile Lys Gly Thr Thr Leu Thr Val Gln Thr Leu Asp Tyr Thr
         115                 120                 125

Leu Gly Gln Gly Trp Leu Ala Gly Asn Asp Thr Ala Pro Arg Glu Val
130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
210                 215                 220

Gly Ala Ile Leu Asn Leu Lys Asn Gly Leu Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265
```

<210> SEQ ID NO 9
<211> LENGTH: 265
<212> TYPE: PRT
<213> ORGANISM: Artificial
<220> FEATURE:
<223> OTHER INFORMATION: Recombinant protein (EP1051495)
<220> FEATURE:
<221> NAME/KEY: misc_feature
<222> LOCATION: (1)..(1)
<223> OTHER INFORMATION: Xaa can be Met or can be deleted

<400> SEQUENCE: 9

```
Xaa Asp Asp Val Thr Cys Ser Ala Ser Glu Pro Thr Val Arg Ile Val
 1               5                  10                  15

Gly Arg Ser Gly Met Arg Val Asp Val Arg Asp Asp Phe His Asp
             20                  25                  30

Gly Asn Gln Ile Gln Leu Trp Pro Ser Lys Ser Asn Asn Asp Pro Asn
         35                  40                  45

Gln Leu Trp Thr Ile Lys Arg Asp Asn Thr Ile Arg Ser Asn Gly Ser
         50                  55                  60

Cys Leu Thr Thr Tyr Gly Tyr Thr Ala Gly Val Tyr Val Met Ile Phe
 65                  70                  75                  80

Asp Cys Asn Thr Ala Val Arg Glu Ala Thr Ile Trp Gln Ile Trp Asp
                 85                  90                  95

Asn Gly Thr Ile Ile Asn Pro Arg Ser Asn Leu Val Leu Ala Ala Ser
             100                 105                 110

Ser Gly Ile Lys Gly Thr Thr Leu Thr Val Gln Thr Leu Asp Tyr Thr
```

```
            115                 120                 125
Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gln Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Val Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Tyr Ala Ile Leu Asn Leu Lys Ser Gly Leu Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265

<210> SEQ ID NO 10
<211> LENGTH: 265
<212> TYPE: PRT
<213> ORGANISM: Artificial
<220> FEATURE:
<223> OTHER INFORMATION: Recombinant protein (EP1051495)
<220> FEATURE:
<221> NAME/KEY: misc_feature
<222> LOCATION: (1)..(1)
<223> OTHER INFORMATION: Xaa can be Met or can be deleted

<400> SEQUENCE: 10

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190
```

```
Cys Leu Thr Ser Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Gly Ala Ile Leu Asn Leu Lys Thr Gly Leu Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265

<210> SEQ ID NO 11
<211> LENGTH: 265
<212> TYPE: PRT
<213> ORGANISM: Artificial
<220> FEATURE:
<223> OTHER INFORMATION: Recombinant protein (EP1051495)
<220> FEATURE:
<221> NAME/KEY: misc_feature
<222> LOCATION: (1)..(1)
<223> OTHER INFORMATION: Xaa can be Met or can be deleted

<400> SEQUENCE: 11

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Gly Thr Ile Arg Ser Asn Gly Ser
50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Gly Ala Ile Leu Asn Leu Lys Lys Gly Pro Ala Met Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265
```

```
<210> SEQ ID NO 12
<211> LENGTH: 265
<212> TYPE: PRT
<213> ORGANISM: Artificial
<220> FEATURE:
<223> OTHER INFORMATION: Recombinant protein (EP1051495)
<220> FEATURE:
<221> NAME/KEY: misc_feature
<222> LOCATION: (1)..(1)
<223> OTHER INFORMATION: Xaa can be Met or can be deleted

<400> SEQUENCE: 12

Xaa Asp Asp Val Thr Cys Ser Ala Ser Glu Pro Thr Val Arg Ile Val
1               5                   10                  15

Gly Arg Asn Gly Met Arg Val Asp Val Arg Asp Asp Phe His Asp
            20                  25                  30

Gly Asn Gln Ile Gln Leu Trp Pro Ser Lys Ser Asn Asn Asp Pro Asn
        35                  40                  45

Gln Leu Trp Thr Ile Lys Arg Asp Gly Thr Ile Arg Ser Asn Gly Ser
    50                  55                  60

Cys Leu Thr Thr Tyr Gly Tyr Thr Ala Gly Val Tyr Val Met Ile Phe
65                  70                  75                  80

Asp Cys Asn Thr Ala Val Arg Glu Ala Thr Ile Trp Gln Ile Trp Asp
                85                  90                  95

Asn Gly Thr Ile Ile Asn Pro Arg Ser Asn Leu Val Leu Ala Ala Ser
            100                 105                 110

Ser Gly Ile Lys Gly Thr Thr Leu Thr Val Gln Thr Leu Asp Tyr Thr
        115                 120                 125

Leu Gly Gln Gly Trp Leu Ala Gly Asn Asp Thr Ala Pro Arg Glu Val
    130                 135                 140

Thr Ile Tyr Gly Phe Arg Asp Leu Cys Met Glu Ser Asn Gly Gly Ser
145                 150                 155                 160

Val Trp Val Glu Thr Cys Asp Ser Ser Gln Lys Asn Gln Gly Lys Trp
                165                 170                 175

Ala Leu Tyr Gly Asp Gly Ser Ile Arg Pro Lys Gln Asn Gln Asp Gln
            180                 185                 190

Cys Leu Thr Ser Gly Arg Asp Ser Val Ser Thr Val Ile Asn Ile Val
        195                 200                 205

Ser Cys Ser Gly Ala Ser Gly Ser Gln Arg Trp Val Phe Thr Asn Glu
    210                 215                 220

Gly Ala Ile Leu Asn Leu Lys Asn Ser Leu Met Val Asp Val Ala Gln
225                 230                 235                 240

Ala Asn Pro Lys Leu Arg Arg Ile Ile Ile Tyr Pro Ala Thr Gly Lys
                245                 250                 255

Pro Asn Gln Met Trp Leu Pro Val Phe
            260                 265
```

MEDICAMENT CONTAINING RECOMBINANT MISTLETOE LECTINS FOR THE TREATMENT OF BRAIN TUMORS

CROSS-REFERENCE TO RELATED APPLICATIONS

This application is a national stage application (under 35 U.S.C. § 371) of PCT/EP2017/053429, filed Feb. 15, 2017, which claims benefit of European Application No. 16155735.0, filed Feb. 15, 2016, both of which are incorporated herein by reference in their entirety.

REFERENCE TO A SEQUENCE LISTING

The instant application contains a sequence listing which has been submitted in ASCII format via EFS-Web and is hereby incorporated by reference in its entirety. Said ASCII copy, created on Aug. 10, 2018, is named 219557_0001_00_US_580558_ST25, and is 32,792 bytes in size.

FIELD OF THE INVENTION

The invention relates to a medicament and/or pharmaceutical composition containing recombinant mistletoe lectins for the treatment of brain tumours, in particular primary brain tumours, gliomas, glioblastomas, meningiomas and pituitary adenomas, and use thereof.

BACKGROUND

Primary brain tumours, such as gliomas, glioblastomas, meningiomas and pituitary adenomas, start from the neuroepithelium, ganglion cells, meninges, nerve sheaths, general nervous supporting tissue or neuroglia and pituitary or ectopic intracranial tissues (germ cell tumours or deformity tumours), and their causes are considered in particular to lie in genetic and hormonal factors, oncogenic viruses, and exogenous carcinogens. They are actual tumours of the central nervous system (CNS) localised in the brain, of varying differentiation and comprising various sub-types, such as: astrocytic tumours, oligodendrogliomas, mixed gliomas (oligoastrocytomas), ependymomas, tumours of the plexus choroideus, retinoblastomas, etc.

The WHO degree of classification is based on dignity: grade I (non-malignant, benign), grade II (semi-benign; postoperative life expectancy 3-5 years), grade III (semi-malignant; postoperative life expectancy 2-3 years), grade IV (malignant; postoperative life expectancy 6-16 months); and frequency: proportion of total or primary brain tumours in all tumour diseases: 7-9% (Kleihues, P., Louis, D. N., Scheithauer, B. W., Rorke, L. B., Reifenberger, G., Burger, P. C., and Cavenee, W. K. (2002) The WHO classification of tumors of the nervous system. J. Neuropathol. Exp. Neurol. 3, 215-225).

A glioma is characterised histologically in (giant cell) (oligo)astrocytoma, oligodendroglioma, mixed gliomas, glioblastoma, and is differentiated depending on growth, such as isomorphic, anaplastic, pilocytic, etc. Sub-groups of gliomas can also be predicted on the basis of the loss of heterozygosity (Smith, J. S., and Jenkins, R. B. (2000) Genetic alterations in adult diffuse glioma: occurrence, significance, and prognostic implications. Front Biosci. 5, 213-231), which lead to a loss of tumour suppressor genes (Tews, B., Felsberg, J., Hartmann, C., Kunitz, A., Hahn, M., Toedt, G., Neben, K., Hummerich, L., von Deimling, A., Reifenberger, G., and Lichter, P. (2006) Identification of novel oligodendroglioma-associated candidate tumor suppressor genes in 1p36 and 19q13 using microarray-based expression profiling. Int J Cancer. 119, 792-800).

In particular, glioblastomas (GBM) are one of the most aggressive brain tumours. The median survival of GBM patients, even with the best therapy preconditions, is only approximately 12-15 months. Natural killer (NK) cells as part of the natural immune system play a key role in the destruction of cancer cells. GBM cells develop strategies for avoiding this killing by down-regulating proteins that are necessary for interaction with NK cells, these being known as danger/stranger protein major histocompatibility complex (MHC), MHC class I polypeptide-related sequence (MIC)-A and -B, or UL16 binding proteins (ULBP) 1, 2, 3, more specifically by means of TGF-$\beta$ mediated immunosuppression. To this end the overexpression of TGF-$\beta$ is an essential feature of GBM, and high concentrations of TGF-$\beta$ can be detected in glioma patients in the cerebrospinal fluid, which is correlated with the growth of the tumour (Kjellman C, Olofsson S P, Hansson O et al: Expression of TGF-beta isoforms, TGF-beta receptors, and SMAD molecules at different stages of human glioma. Int J Cancer 2000; 89: 251-258). In addition, TGF-$\beta$ is responsible for the down-regulation of MHC expression, increasing the differentiation of naïve cells in T-reg cells, blocking dendritic cell maturation, and inducing cell death of K and T-cells (Eisele G, Wischhusen J, Mittelbronn M et al.: TGF-beta and metalloproteinases differentially suppress NKG2D ligand surface expression on malignant glioma cells. Brain 2006; 129: 2416-2425, Platten M, Wick W, Weller M: Malignant glioma biology: role for TGF-beta in growth, motility, angiogenesis, and immune escape. Microsc Res Tech 2001; 52: 401-410).

There is thus a great need to provide medicaments for the treatment and prophylaxis of brain tumours, in particular primary brain tumours, such as gliomas, glioblastomas, meningiomas and pituitary adenomas.

Mistletoe extracts have been used therapeutically for hundreds of years. In particular in cancer therapy, mistletoe preparations have been used with varying levels of success (Bocci V 1993 J Biol Regulators and Homeostatic Agents 7(1): 1-6; Gabius H-J, Gabius S, Joshi S S et al. 1993 Planta Med 60: 2-7; Gabius H-J & Gabius S 1994 PZ 139: 9-16; Ganguly C & Das S 1994 Chemotherapy 40: 272-278, Hajto T, Hostanska K, Gabius H_J 1989 Cancer Res 49: 4803-4808, Hajto T, Hostanska K, Frei K et al. 1990 Cancer Res. 50: 3322-3326). It has been found that the therapeutic effects are conveyed in particular by what are known as mistletoe lectins (viscumins, *Viscum album* Agglutinine, VAA). Mistletoe lectin, besides a cytotoxic effect, also brings about non-specific immunostimulation, the positive effects of which are used for therapy in tumour patients. Various studies with mistletoe lectin in vitro (Hajto et al., 1990 (supra); Mannel D N, Becker H, Gundt A et al. 1991 Cancer Immunol Immunother 33: 177-182; Beuth J, Ko K L, Tunggal L et al. 1993 Drug Res 43: 166-169) and in vivo (Hajto T 1986 Oncology 43 suppl 1: 51-65; Hajto et al., 1989 (supra), Beuth J, Ko H L, Gabius H-J et al. 1991 In Vivo 5: 29-32; Beuth J, Ko H L, Gabius H-J et al. 1992 J Clin Invest 70: 658-661), and clinical studies (Beuth et al., 1992 (supra)) have demonstrated an increased release of inflammatory cytokines (TNF-alpha, IL-1, IL-6) and an activation of cellular components of the immune system (TH-cells, NK-cells, B- and T-lymphocytes) (Braedel-Ruoff S: Immunomodulatory effects of *Viscum album* extracts on natural killer cells: review of clinical trials. Forsch Komplementmed 2010; 17: 63-73, Gren A: Effects of Iscador preparations on the reactivity of mouse immune system. Neuro Endocrinol Lett 2009; 30: 530-534, Lee C H, Kim J K, Kim H Y et al.: Immunomodulating effects of Korean mistletoe lectin in vitro and in vivo. Int Immunopharmacol 2009; 9: 1555-1561, Nikolai G, Friedl P, Werner M et al: Effect of a mistletoe extract (Iscador QuFrF) on viability and migratory behavior of human peripheral CD4+ and CD8+ T lymphocytes in three-dimensional collagen lattices. In Vitro Cell Dev Biol Anim 1997; 33: 710-716).

By analysis of the mistletoe extract, it has been possible thus far to identify three mistletoe lectins (ML-I, ML-II, ML-III) having different molecular weights and sugar-binding specificities. It has been found that the immunostimulating effect of the mistletoe extract on can be attributed to ML-I. The ML-I lectin consists of two glycosylated A- and B-chains (MLA and MLB). The A-chain is responsible for enzymatic inactivation of ribosomes (Endo Y, Tsurugi K & Franz H 1988 FEBS Lett 231: 378-380), whereas the B-chain is involved in carbohydrate bonding. The two chains are linked to one another by disulphide bridges. The resultant mistletoe lectin monomers can clump together to form dimers, with formation of non-covalent bonds.

It is possible to produce the biologically active mistletoe lectin advantageously recombinantly. EP 0751221 describes the preparation of mistletoe lectin polypeptides in a pure state as a structurally homogenous substance, wherein, proceeding from the gene sequence of mistletoe lectin, recombinant, highly pure individual chains (A-chain, B-chain) are produced, which can be re-associated in vitro and thus provide a recombinant mistletoe lectin holoprotein, which is homogeneous in respect of its protein chemistry, enzymatically and structurally, also known as Aviscumine. According to EP 0751221 the recombinant mistletoe lectin polypeptide is suitable as holoprotein and as sub-chain and in the form of sub-fragments for therapeutic purposes and is included within the scope of the invention.

Document WO2012104355A1 also describes the antiviral effect of recombinant mistletoe lectins. WO2012136857A1 discloses the treatment of skin cancer, in particular of a malignant melanoma also in the form of a metastasising tumour by means of recombinant mistletoe lectins.

Previously, recombinant mistletoe lectins were used advantageously in the treatment of tumour diseases. The use of recombinant mistletoe lectins for the treatment of brain tumours however, in particular primary brain tumours, such as gliomas, glioblastomas, meningiomas and pituitary adenomas, is not described in the prior art.

In the prior art, Podlech et al (Podlech O, Harter P N, Mittelbronn M et al.: Fermented mistletoe extract as a multimodal antitumoral agent in gliomas. Evid Based Complement Alternat Med 2012: 501796) describes the use of ISCADOR—a fermentatively obtained mistletoe extract—as growth inhibitor for GBM and indicates the antitumoral suitability of ISCADOR for the treatment of GBM.

Lenartz (Lenartz et al., Immunoprotective Activity of the Galactoside-Specific lectin from mistletoe after Tumor Destructive Theraly in Glioma Patients, Anticancer Research 16: 3799-3802 (1996)) reports on a mistletoe extract (ML-1) for the treatment of glioma patients, wherein the mistletoe extracts have a specific glycosylation.

The plant-based mistletoe lectins described in the prior art—whether or not obtained from fermentatively or non-fermentatively produced mistletoe extracts—are inhomogeneous (Soler M H, Stoeva S, Schwamborn C et al. 1996 FEBS Letter 399: 153-157, Soler H S, Stoeva S, Voelter W 1998 Biochem Biophys Res Comm 246: 596-601) and differ from one another non-uniformly in respect of their effect (EP 1051495 B1), and are not effective per se as active substance or as immunomodulator. Thus, the mistletoe lectin obtained from Korean mistletoe (*Viscum album colaratum*) for example should be assigned to the RIP II proteins, but has significant structural differences in the structure and conformation compared to the recombinant mistletoe lectin discussed here (Kang T B, Song S K, Yoon T J et al. 2007 J Biochem Mol Biol 40(6): 959-965). It is particularly disadvantageous that no exact dose adjustment is possible and that mistletoe lectins obtained from plant-based fermentatively or non-fermentatively produced extracts comprise impurities. Furthermore, the mistletoe lectins obtained from plant extracts—produced fermentatively or non-fermentatively—present differences in the glycosylation which influence the efficacy (in particular kinetics, etc.). Apart from this, the production of each new mistletoe extract batch yields a product that is not identical to the previous batch, with different contents of its ingredients including the glycosylated mistletoe lectins.

BRIEF SUMMARY OF THE INVENTION

The invention relates to a medicament and/or pharmaceutical composition containing recombinant mistletoe lectins for the treatment of the brain tumours, in particular primary brain tumours, gliomas, glioblastomas, meningionas and pituitary adenomas, and use thereof.

DETAILED DESCRIPTION

The recombinant mistletoe lectins according to the invention advantageously do not have any such glycosylation, are absolutely pure, and can be produced reproducibly.

Surprisingly, it could now be found that recombinant mistletoe lectins not only have the aforesaid advantages, such as improved reproducibility, homogeneity and adjustable dosing, but provide improved NK cell cytotoxicity compared to a plant-based or fermentative mistletoe extract from the prior art via the NK cell surface marker NKG2D and are therefore particularly suitable for the treatment of brain tumours, gliomas, glioblastomas, meningiomas and pituitary adenomas. Recombinant mistletoe lectins also demonstrate a specific and advantageous anti-migratory effect on brain tumour cells.

Natural killer (NK) cells as constituents of the natural immune system play a key role in the destruction of cancer cells. In order to achieve destruction of tumour cells by NK cells, the docking of NK cells to tumour cells is necessary. Here, the NKG2d receptors on NK cells and for activation of necessary surface proteins (NKp30, NKp44, NKp46) play an important role. In the examples, the effect of the recombinant mistletoe lectins is compared with the effect of the fermented mistletoe extract ISCADOR Q on the interaction of NK cells with the GBM cell LNT0229-Luc.

The object of the present invention thus lies in providing a medicament and pharmaceutical agent for the treatment of brain tumours, in particular primary brain tumours, such as gliomas, glioblastomas, meningiomas and pituitary adenomas.

The object is achieved by providing a medicament and a pharmaceutical composition, wherein these contain recombinant mistletoe lectins for the treatment of brain tumours, in particular primary brain tumours, such as gliomas, glioblastomas, meningiomas and pituitary adenomas.

The medicament according to the invention preferably comprises the mistletoe lectin A chain (MLA) or the mistletoe lectin B chain (MLB), in each case individually or together, also in the form of dimers (see for example EP 0 751 221 or EP 1 051 495).

The recombinant mistletoe lectin polypeptide of the mistletoe lectin A chain comprises the following sequences: SEQ ID No. 1-3, inclusive of the isoforms thereof or a functional fragment thereof.

The recombinant mistletoe lectin polypeptide of the mistletoe lectin B chain comprises the following sequences: SEQ ID No. 4-12, inclusive of the isoforms thereof or a functional fragment thereof (hereinafter all "recombinant mistletoe lectins").

More preferably, a recombinant mistletoe lectin according to the invention is a heterodimer consisting of the sequences SEQ ID No. 1 and SEQ ID No. 4, see for example EP 0 751 221 (what is known as Aviscumine).

The term "functional fragment" in conjunction with this invention defines fragments or the aforesaid polypeptides which have the same biological function as the polypeptide presented above with the corresponding amino acid sequence.

The term "same biological function" in this context for example describes the fact that fragments or derivatives of the polypeptides induce the same signals in a cell as the aforesaid peptides. Examples of fragments are peptide domains with defined functions. The "same biological function" also comprises the cytotoxicity, immunostimulation (both of the native and adaptive immune system), stimulation of the expression or the activation of surface markers, the induction of apoptosis, or endorphin stimulation.

The term "biological activity of the recombinant mistletoe lectin" is understood here to mean any biological activity from the spectrum of all biological activities of the recombinant mistletoe lectin. A function of this kind is for example the pharmacological effect of the recombinant mistletoe lectin.

Studies of ML-I monomers have revealed 25 isoforms, which can be attributed to different combinations of various A- and B-chains and different states of glycosylation of the chains.

For the present invention, a mistletoe lectin polypeptide or a fragment thereof, comprising the sequence variability of the various MLA and MLB chains, with sequences SEQ ID No. 1-12 is considered in accordance with the invention.

The medicament according to the invention contains a recombinant mistletoe lectin polypeptide with the sequences SEQ ID No. 1-12 or a functional fragment thereof or any combination thereof.

It is also preferred that the use of recombinant mistletoe lectins according to the invention takes effect in patient populations that do not respond to tumour preparations by means of standard therapy or that comprise non-responders or therapy failures.

The invention therefore comprises patients or patient populations of non-responders and therapy failures for the treatment of brain tumours, in particular primary brain tumours, such as gliomas, glioblastomas, meningiomas and pituitary adenomas, in which standard tumour therapy is unsuccessful.

The term "brain tumour" in accordance with the invention comprises primary brain tumours, such as gliomas, meningiomas and pituitary adenomas, starting from the neuroepithelium, ganglion cells, meninges, nerve sheaths, general nervous supporting tissue or neuroglia and pituitary or ectopic intracranial tissues (germ cell tumours or deformity tumours), and their causes are considered in particular to lie in genetic and hormonal factors, oncogenic viruses, and exogenous carcinogens.

A preferred embodiment according to the invention, however, is the treatment of gliomas (see for example the description of the indications in Pschyrembel®, $266^{th}$ edition 2014, De Gruyter Verlag, Berlin).

The invention additionally relates to a medicament for the treatment of brain tumours, in particular primary brain tumours, such as gliomas, glioblastomas, meningiomas and pituitary adenomas, which contains the recombinant mistletoe lectin polypeptide optionally together with a pharmaceutically acceptable carrier, thus forming a pharmaceutical composition. Examples of particularly suitable pharmacologically acceptable carriers are known to a person skilled in the art of tumour medicine and comprise buffered saline solutions, water, etc., various kinds of detergents, sterile solutions, etc. Medicaments that comprise such carriers can be formulated by means of known conventional methods. These medicaments can be administered to an individual in a suitable dose. The administration can be implemented locally, orally or parenterally, for example intravenously, intraperitoneally, subcutaneously, intramuscularly, locally, intranasally, intrabronchially or intradermally, or via a catheter at a point in an artery. The kind of dosing if determined by the treating doctor in accordance with the clinical factors. It is known to a person skilled in the art that the kind of dosing is dependent on various factors, such as body size or weight, body surface, age, sex, or general health of the patient, but also on the specific agent to be administered, the duration and kind of administration, and any other medicaments that might be administered in parallel.

The pharmaceutical composition comprising the recombinant mistletoe polypeptides according to the invention can be administered locally or systemically.

A dosing of the mistletoe lectins according to the invention for human use of 2-10 ng/kg (body weight) has proven to be advantageous. The dosing particularly advantageously lies in a range of 3-7 ng/kg. The administered amount is preferably 5 ng/kg body weight. The preferred human dosing not based on body weight is 350 ng.

The medicament according to the invention is applied over a period of time of at least 8 weeks at a frequency of 1× daily to 1× weekly. The medicament is preferably administered 2 to 3× weekly, particularly preferably 2× weekly.

The invention therefore relates to a method for dosing the recombinant mistletoe lectins according to the invention or the medicament according to the invention, wherein the dosing is 2 to 10 ng/kg (body weight). In particular, the invention relates to a method for dosing the recombinant mistletoe lectins according to the invention or the medicament according to the invention, wherein the dose is 200-500 ng, in particular 350 ng, and is administered to the patient at least 1× weekly.

The following examples and drawings serve to explain the invention, but the invention is not limited to these examples.

EXAMPLES AND DRAWINGS

Example 1 of a Composition of the Medicament

Solution for injection: 1 mL ampoule with 0.5 mL to 1.0 mL injection solution

| | |
|---|---|
| Aviscumine | 200-500 ng |
| Sodium monohydrogen phosphate dihydrate | 2.8 mg-5.6 mg |
| Sodium dihydrogen phosphate dihydrate | 0.078 mg-0.155 mg |
| Sodium chloride | 3.3 mg-6.7 mg |
| Polyoxyethylene sorbitan ester (polysorbate) | 0.1 mg |
| Glutaminic acid | 0.1 mg |
| Water for injection | ad 0.5 ml to ad 1.0 mL |

Example 2 of a Composition of the Medicament

Powder for preparation of a solution or injection, 2R glass vial with

| | |
|---|---|
| Aviscumine | 200-500 ng |
| Trehalose | 40.0 mg |
| Sodium chloride | 1.0 mg |
| Tris(hydroxymethyl)aminomethane (TRIS) | 0.6 mg |
| Polyoxyethylene sorbitan ester (polysorbate) | 0.1 mg |

Hydrochloric acid to adjust the pH value for administration, the powder is dissolved with 0.5 mL or 1.0 mL water for injection.

Example 3

Method: LNT-229-Luc cells grow in DMEM (Sigma, Taufkirchen, Germany) medium with 10% foetal calf serum and penicillin/streptomycin in a humid atmosphere enriched with 5% CO2.

For isolation of the NK cells, PBMC was taken from the blood of healthy donors and co-cultivated with irradiated RPMI 8866 feeder cells (ATCC, USA) in RPMI medium (Sigma, Taufkirchen, Germany) in order to obtain polyclonal NK cell populations. The NK cells are purified with the aid of an NK cell isolation kit (Miltenyi Biotec, Bergisch Gladbach, Germany) >98%. Their lytic activity in relation to GBM cells is determined via the Luciferase activity measurement. For the inactivation of the NK cell activity, the NK cells are pre-incubated with antibodies against NKG2D (BioLegend, Fell, Germany) for 30 minutes prior to their 4-hour co-cultivation (effector/target cell 20:1) with the GBM cells. The GBM cells are in turn pre-treated for 24 h with Aviscumine or ISCADOR Q prior to the co-cultivation with the NK cells and are washed in the co-culture prior to their use.

Result: Aviscumine influences the effect of NK cells on the GBM cell by intensifying the interaction of their receptor NKG2D with the target cell.

The blocking of the NKG2D receptor by antibody leads, as expected, to a reduction of the lysis conveyed by NK cells by 52% in the control group (medium); Aviscumine antagonises the effect of the antibody in part: The lysis conveyed by NK cells is therefore reduced only by 38% by the antibody. A comparison with the fermented mistletoe extract ISCADOR Q was not possible under these conditions, since with the same mistletoe lectin-based concentration of 8 ng/ml, the GBM cells without influence of NK cells are lysed to a much greater extent than conveyed by the control. Clearly, further ingredients of the fermented extract are directly cytotoxic (Table).

| | GBM cell lysis | | |
|---|---|---|---|
| | Without antibody treatment | anti-NKG2D pre-treatment | |
| Medium | 67% | 32.1% (Inhibition: d. lysis by 52.1%) | P < 0.05 |
| Aviscumine | 68.4% | 42.6% (Inhibition: d. lysis by 37.7%) | P < 0.05 |
| Iscador Q | 83.2% | 61.6% | not significant |

According to Podlech, ISCADOR Q (200 mg) is diluted 2000 times for incubation experiments (100 micrograms/ml). The extract contains, inter alia, various mistletoe lectins, the content of which in the used batch is stated as 15.050 micrograms mistletoe lectin/ml. This means a mistletoe lectin concentration of 7.5 nanograms lectin per ml in the incubation experiments. The concentration of 7.5 nanogram lectins per ml leads after 48 h to an inhibition of growth of almost 20-30% in LNT-229 and SMA560 glioma cells.

ISCADOR Q inter alia also contains various cytotoxic viscotoxins, the content of which in the used batch is stated as 364 micrograms viscotoxin/ml. This means a viscotoxin concentration of 182 nanograms viscotoxins per ml incubation solution.

When using ISCADOR it is therefore unclear which of the numerous ingredients is responsible for the inhibition of growth of LNT-229 and SMA560 glioma cells.

The recombinant mistletoe lectin Aviscumine inhibits the growth of various brain tumour cells by 100% in a concentration range of 0.4-11 ng/ml and as an inhibitor of brain tumour cells is thus >10 times more potent than ISCADOR Q. If it is desired to attribute the effect of ISCADOR Q to the mistletoe lectins contained therein, mistletoe lectin-antagonising ingredients must thus be assumed in the fermented extract. Other fluctuating constituents of mistletoe extracts are also cytotoxic (see Eggenschwiler J, von B L, Stritt B, Pruntsch D, Ramos M, Urech K, Rist L, Simoes-Wust A P, Viviani A; Mistletoe lectin is not the only cytotoxic component in fermented preparations of *Viscum album* from white fir (*Abies pectinata*). BMC Complement Altern Med 2007, 7:14).

Example 4

The human glioma cell line LNT-229 was incubated for 24 h with the mistletoe lectin-containing extract Iscador Qu, Aviscumine and native mistletoe lectin I. The used concentrations corresponded to 8 ng ML-I/ml. After 24 h the cells were washed for removal of the active substances, and in each case 20,000 cells were applied in a cell migration chamber (Boyden Chamber) to the upper layer of a polycarbonate membrane, which on account of its 8 mm pores is permeable for the cells and which divides the chamber into an upper and lower compartment. Cells that have migrated through the membrane either remain adhered to the underside of the membrane depending on their adherent properties (content of pro-migratory or anti-migratory proteins) or pass into the buffer located in the lower compartment.

Figure 1:
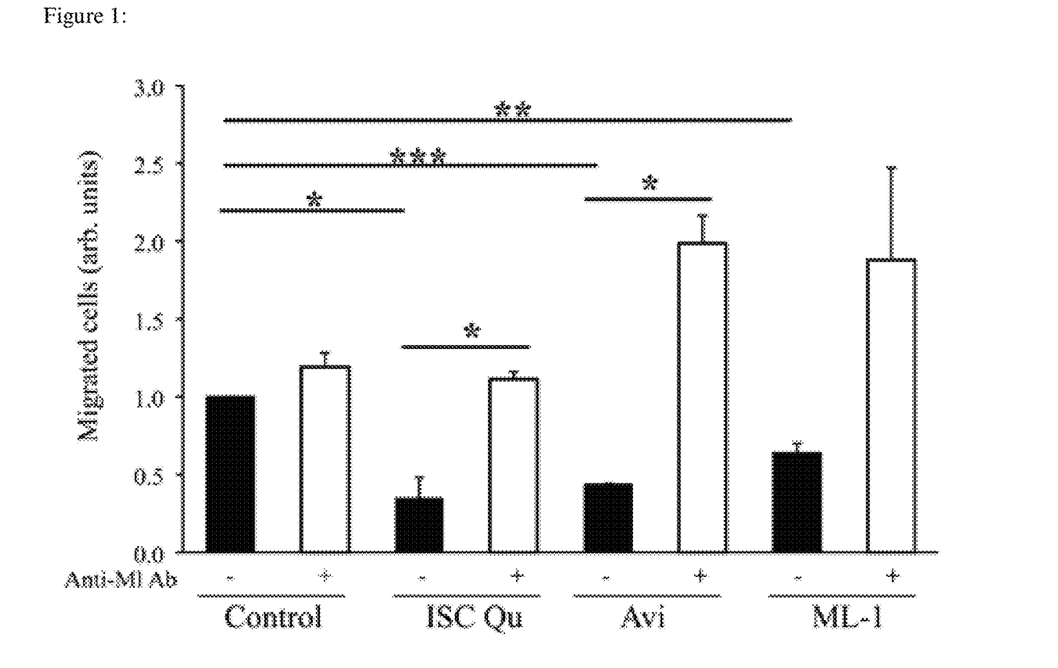
FIG. 1 depicts a graph of the number of migrated cells as a function of incubation treatment of human gliomacells. ISC Qu: ISCADOR Q. Avi: Aviscumine. ML-1: mistletoe lectin I. Anti-M1 Ab: mistletoe lectin antibody.

At the end of the experiment the membrane can be removed, and the adhering cells stained and counted. The difference between cell count and adhering cells is the number of migrated cells. The results are shown in FIG. 1.

Compared to an untreated control group, the number of migrating cells reduces on account of the mistletoe lectin effect. Antibodies against mistletoe lectin cancel the effect.

The strongest anti-migratory effect is attained by Aviscumine (supra) (p<0.001).

Figure 2:
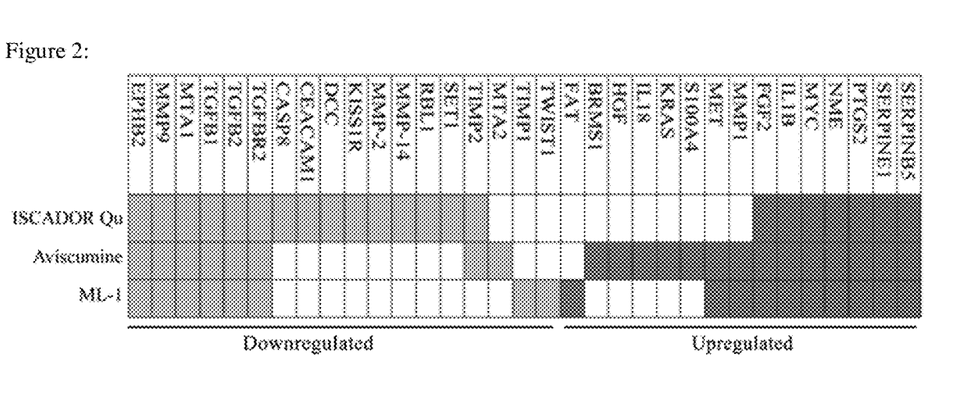
FIG. 2 depicts a comparative heat map of upregulated and downregulated genes as a function of treatment with ISCADOR Qu, Aviscumine, or ML-1.

This data, therefore that Aviscumine presents the strongest effect, can be explained by the specific downregulation of the pro-migratory genes MTA1 and MTA2 and the upregulation of the anti-migratory genes BRMS1 and SERPINB5. These genes, in contrast to the other mistletoe lectin preparations, can be downregulated and upregulated only by Aviscumine (see comparative heat map in FIG. 2).

The invention claimed is:

1. A method of treating a brain tumor comprising administering to a human patient with a brain tumor a drug containing recombinant mistletoe lectin, wherein the recombinant mistletoe lectin is selected from the group of amino acid sequences SEQ ID No. 1-12 or a combination thereof.

2. The method of claim 1, wherein the recombinant mistletoe lectin polypeptide is a mistletoe lectin A, selected from the group of amino acid sequences SEQ ID No. 1-3 or a combination thereof.

3. The method of claim 1, wherein the recombinant mistletoe lectin polypeptide is a mistletoe lectin B, selected from the group of amino acid sequences SEQ ID No. 4-12 or a combination thereof.

4. The method of claim 1, wherein the human patient is a non-responder to standard tumor therapy or has had a therapeutic failure of standard tumor therapy.

5. The method of claim 1, wherein the medicament is combined with at least one of a pharmaceutically acceptable carrier or further auxiliaries and additives.

6. The method of claim 1, wherein the drug is administered to the human patient in a dosage in a range of 3-7 ng recombinant mistletoe lectin per kg of body weight.

7. The method of claim 6, wherein the drug is administered in a dosage of 5 ng recombinant mistletoe lectin per kg of body weight.

8. The method of claim 1, wherein the drug is administered to the human patient in a dosage of 200-500 ng recombinant mistletoe lectin regardless of body weight of the human patient.

9. The method of claim 8, wherein the dosage of recombinant mistletoe lectin is 350 ng regardless of body weight of the human patient.

10. The method of claim 1, wherein the medicament is administered at least once a week, at least twice a week, or at least three times per week.

11. The method of claim 1, wherein the brain tumor is selected from the group consisting of a primary brain tumor, a glioma, a glioblastoma, a meningioma, and a pituitary adenoma.

* * * * *